United States Patent

Masaki et al.

[11] Patent Number: 4,891,433
[45] Date of Patent: Jan. 2, 1990

[54] PROCESS FOR THE PREPARATION OF DIBENZOTHIEPIN DERIVATIVE

[75] Inventors: Mitsuo Masaki, Chiba; Hiromitsu Takeda, Kitakatsushika; Naoya Moritoh, Kuki; Toshihiro Takahashi, Misato, all of Japan

[73] Assignee: Nippon Chemiphar Co., Ltd., Japan

[21] Appl. No.: 102,981

[22] Filed: Sep. 30, 1987

[30] Foreign Application Priority Data

Jun. 10, 1986 [JP] Japan .................................. 61134682
Jun. 21, 1986 [JP] Japan .................................. 61-145641
Jul. 2, 1986 [JP] Japan .................................. 61-155432

[51] Int. Cl.$^4$ .................... C07D 337/14; C07C 149/40
[52] U.S. Cl. .......................................... 549/12; 560/9; 560/152; 560/153; 562/431
[58] Field of Search ...................... 549/12; 560/9, 152, 560/153; 562/431

[56] References Cited

U.S. PATENT DOCUMENTS 4,247,706 1/1981 Fujimoto et al. ..................... 549/12

OTHER PUBLICATIONS

Patent Abstracts of Japan, vol. 7, No. 213, p. 132.
Patent Abstracts of Japan, vol. 6, No. 197, p. 54.
Streitwieser & Heathcock, *Introduction to Organic Chemistry*, pp. 766–767.

Primary Examiner—Mary C. Lee
Assistant Examiner—Mary Sue Howard
Attorney, Agent, or Firm—Sixbey, Friedman, Leedom & Ferguson

[57] ABSTRACT

A novel process for the preparation of 2-(10,11-dihydro-10-oxodibenzo[b, f]thiepin-2-yl)propionic acid which shows high anti-inflammatory and analgetic action is disclosed. The process starts from a propiophenone derivative having the formula (II):

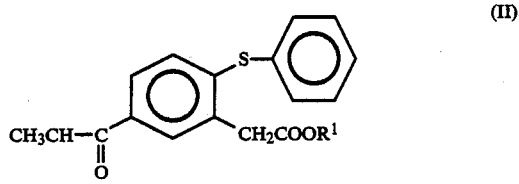

wherein $R^1$ is hydrogen or a lower alkyl group, which is once converted into a haloacetal compound via a halo-ketone compound, and then converted into the desired dibenzothiepin derivative through a combination of rearrangement, hydrolysis and ring closure in variable sequences.

23 Claims, No Drawings

PROCESS FOR THE PREPARATION OF DIBENZOTHIEPIN DERIVATIVE

BACKGROUND OF THE INVENTION

1. Field of the Invention

The present invention relates to a process for the preparation of 2-(10,11-dihydro-10-oxodibenzo[b,f]thiepin-2-yl)propionic acid which is of value as a pharmaceutically acitive compound.

2. Description of prior art

It is known that 2-(10,11-dihydro-10-oxodibenzo[b,f]-thiepin-2-yl)propionic acid having the following formula (I):

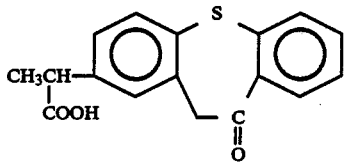

(hereinafter refers to as dibenzothiepin derivative) shows a high anti-inflammatory action as well as a high analgetic action. The dibenzothiepin derivative is further known as a practically valuable anti-inflammatory agent with littel side effect. For example, the dibenzothiepin derivative and its pharmacological actions are described in Japanese Patent Provisional Publication No. 55(1980)-53282.

The above-mentioned Patent Provisional Publication discloses a process for the preparation of the dibenzothiepin derivative wherein 3-(α-cyanoethyl)-6-phenylthiophenylacetic acid is cyclized to give a dibenzothiepinpropionamide derivative and this derivative is then hydrolyzed.

Another process for preparing the dibenzothiepin derivative is disclosed in Japanese Patent Provisional Publication No. 57(1982)-106678. This process comprises hydrolysis of a phenylacetate ester having a nitrile group to give a dicarboxylic acid derivative and subsequent ring closure of the dicarboxylic acid derivative in the presence of a condensing agent such as sulfuric acid or polyphosphoric acid.

Another process for preparing the dicarboxylic acid derivative is disclosed in Japanese Patent Provisional Publication No. 58(1983)-113168 which comprises a propiophenone derivative is once converted into a hydroxyacetal compound. This process can be illustrated by the following equation:

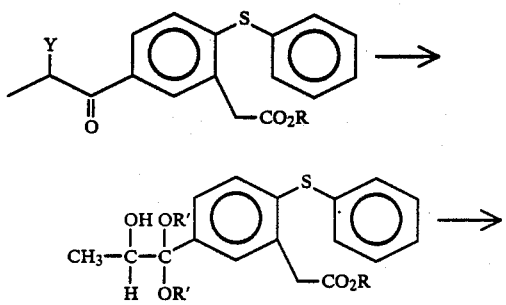

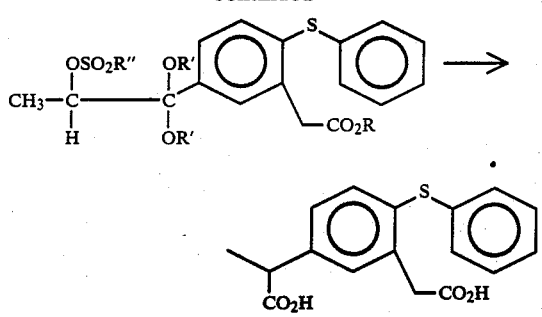

wherein Y is chlorine or bromine, R is an alkyl group having 1-5 carbon atoms or hydrogen, R' is an alkyl group having 1-5 carbon atoms, and R" is methyl or p-tolyl.

While the these known processes are employable for the preparation of the dibenzothiepin derivative, these processes have drawbacks in that the processes involve complicated and multiple steps or the use of a toxic reagent such as KCN. Accordingly, these known processes are not favorable as industrially employable processes.

SUMMARY OF THE INVENTION

It is an object of the present invention to provide an improved process for the preparation of 2-(10,11-dihydro-10-oxodibenzo[b,f]thiepin-2-yl)propionic acid.

It is another object of the invention to provide a process for the preparation of 2-(10,11-dihydro-10-oxodibenzo[b,f]thiepin-2-yl)propionic acid, which is free from the use of a toxic reagent and does not involve complicated steps.

It is a further object of the invention to provide a process for preparing 2-(10,11-dihydro-10-oxodibenzo[b,f]thiepin-2-yl)propionic acid in an improved high yield.

There is provided by the present invention a process for the preparation of 2-(10,11-dihydro-10-oxodibenzo[b,f]thiepin-2-yl)propionic acid of the formula (I):

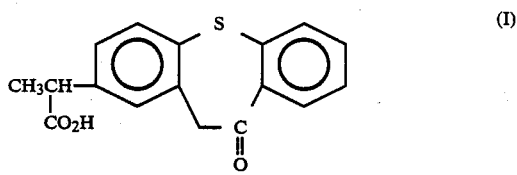

which comprises the steps:

reacting a propiophenone derivative having the formula (II):

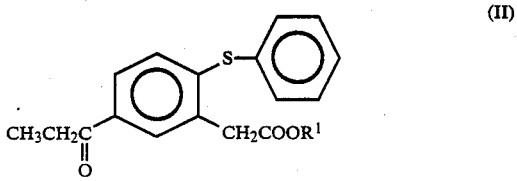

wherein $R^1$ is hydrogen or a lower alkyl group, with a halogenating agent to form a haloketone compound having the formula (III):

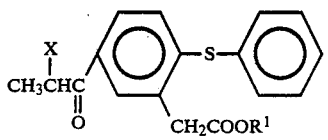 (III)

wherein R¹ has the same meaning as defined above; reacting the haloketone compound with a primary alcohol having the formula (IV):

 (IV)

wherein R² is a lower alkyl group, and an orthoformate having the formula (V):

 (V)

wherein R² has the same meaning as defined above, to form a haloacetal compound having the formula (VI):

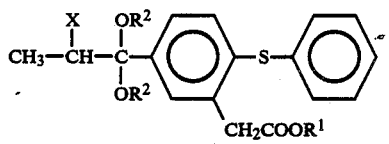 (VI)

wherein R¹ and R² both have the same meanings as defined above, and R¹ is the same as R² where R¹ of the formula (II) is hydrogen, and X is a halogen atom; converting the haloacetal compound in the presence of a zinc halide into a dicarboxylic acid ester having the formula (VII):

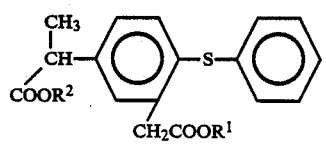 (VII)

wherein R¹ and R² both have the same meanings as defined above; and hydrolyzing the dicarboxylic acid ester to give a dicarboxylic acid having the formula (VIII):

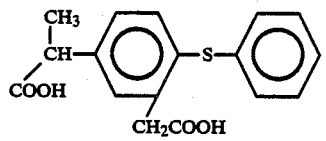 (VIII)

and
converting the dicarboxylic acid in the presence of a condensing agent into the dibenzothiepin derivative of the formula (I).

Further, 2-(10,11-dihydro-10-oxodibenzo[b,f]thiepin-2-yl)propionic acid can be also obtained by the same process as above except that the above-mentioned dicarboxylic acid ester of the formula (VII) is first cyclized in the presence of a condensing agent to give a dibenzothiepin ester derivative which is then converted into the desired dibenzothiepin derivative by hydrolysis. In more detail, the dibenzothiepin derivative of the formula (I) can be obtained by the process comprising the steps of:

converting the dicarboxylic acid ester having the formula (VII):

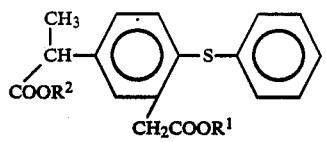 (VII)

wherein R¹ and R² both have the same meanings as defined above; in the presence of a condensing agent into a dibenzothiepin ester derivative having the formula (IX):

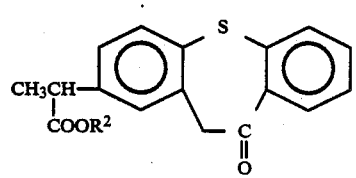 (IX)

wherein R² has the same meaning as defined above, and
hydrolyzing the dibenzothiepin ester derivative to give the dibenzothiepin derivative of the formula (I).

Furthermore, 2-(10,11-dihydro-10-oxodibenzo[b,f]-thiepin-2-yl)propionic acid can be also obtained by the same process as above except that the above-mentioned haloacetal compound of the formula (VI) is directly converted into the dicarboxylic acid of the formula (VIII). In more detail, the dibenzothiepin derivative of the formula (I) can be obtained by the process comprising the steps of:

converting the haloacetal compound having the formula (VI):

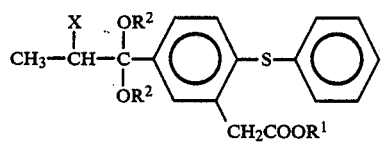 (VI)

wherein R¹ and R² both have the same meanings as defined above, and R¹ is the same as R² where R¹ of the formula (II) is hydrogen, and X is a halogen atom; in a proton-donating medium in the presence of a basic compound into a dicarboxylic acid having the formula (VIII):

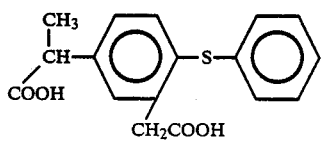 (VIII)

and
converting the dicarboxylic acid in the presence of a condensing agent into the dibenzothiepin derivative of the formula (I).

PREFERRED EMBODIMENT OF THE INVENTION

In the formulae of the compounds employed for the preparation of the dibenzothiepin derivative according to the present invention, each of $R^1$ and $R^2$ is the same as or different from each other and is an alkyl group having 1-6 carbon atoms, preferably methyl or ethyl. $R^1$ may be hydrogen in the propiophenone derivative of the formula (II). In this case, $R^1$ in the formulae (VI) and (VII) generally is the same as $R^2$ of the same formula.

The first step of the process of the invention is for converting a propiophenone derivative of the formula (II) to a haloketone compound of the formula (III) using a halogenating agent.

As the halogenating agent, a brominating agent or a chlorinating agent is generally employed. Preferred is the brominating agent, particularly, bromine.

The halogenating agent is employed in an amount of at least one mole per one mole of the propiophenone derivative.

The reaction is preferably carried out at a temperature in the range of room temperature to 60° C. for a period of 0.5 to 48 hours. The reaction can be carried out in a solvent such as methanol, ethanol, ethylene tetrachloride, carbon tetrachloride, benzene, and toluene which does not participate in the reaction.

The second step is for converting the haloketone compound of the formula (III) into the haloketal compound of the formula (VI) using a primary alcohol of the formula (IV) and an orthoformate of the formula (V).

Preferred examples of the primary alcohols include methyl alcohol and ethyl alcohol. Preferred examples of the orthoformates include methyl orthoformate and ethyl orthoformate.

The orthoformate ester and primary alcohol are used in amounts of at least two moles and at least one mole, respectively, per one mole of the haloketone derivative. A great amount of the primary alcohol or orthoformate can be employed for further serving as a reaction solvent.

The reaction is preferably carried out at a temperature in the range of 80° to 130° C. for a period of 0.5 to 48 hours. The reaction can be carried out in a solvent such as ethylene tetrachloride, carbon tetrachloride, benzene, and toluene which does not participate in the reaction.

As noted hereinbefore, if the $R^1$ of the formula (III) (propiophenone derivative) is hydrogen, the hydrogen generally is replaced with $R^2$ of the primary alcohol in the reaction.

If desired, the first step and the second step can be continuously performed without isolating the product of the first step, namely, the haloketone compound of the formula (III). In this process, the continuous reaction can be carried out by reacting the propiophenone derivative with the halogenating agent, primary alcohol and orthoformate.

The third step is for converting the haloacetal compound of the formula (VI) in the presence of a zinc halide into a dicarboxylic acid ester of the formula (VII).

This rearrangement reaction is generally carried out in a solvent such as toluene, methyl alcohol, methyl orthofomate, dichloroethane or trichloroethane which does not participate in the reaction at a temperature of from room temperature to refluxing temperature for a period of 0.5 to 24 hours.

An preferred example of the zinc halide is zinc bromide. The zinc halide can be prepared in situ in the reaction solution from zinc metal. Hydrogen halide produced in the reaction reacts with the zinc metal to prepare a zinc halide.

The zinc halide is preferably employed at least in a catalystic amount.

If desired, the second step and the third step can be continuously performed without isolating the product of the second step, namely, the haloketal compound of the formula (VI). In this process, the continuous reaction can be carried out by reacting the haloketone compound with the primary alcohol and orthoformate, and then further heating the reaction mixture after addition of the zinc halide.

Alternatively, the first step, the second step and the third step can be combined for directly converting the propiophenone derivative into the dicarboxylic acid ester without isolating the haloketone compound and haloacetal compound. In this process, the continuous reaction can be carried out by first reacting the propiophenone derivative, halogenating agent, primary alcohol and orthoformate and then further heating the reaction mixture after addition of the zinc halide.

The fourth step is for converting the dicarboxylic acid ester of the formula (VII) into a dicarboxylic acid of the formula (VIII) through hydrolysis.

The hydrolysis can be carried out in a conventional manner, for instance, by heating the dicarboxylic acid ester in an aqueous alkaline solution or in an aqueous acidic solution.

The fifth step is for converting the dicarboxylic acid of the formula (VIII) into the dibenzothiepin derivative of the formula (I) in the presence of a condensing agent. Accordingly, this reaction is a ring closure reaction.

The condesing agent is preferably employed in a weight amount of 1-30 times as much as the weight amount of the dicarboxylic acid. Examples of the condensing agents include sulfuric acid, polyphosphoric acid (preferably, 105%, 116%, or their mixture) and polyphosphoric acid ester. The reaction is generally carried out at a temperature of from room temperature to 150° C. for a period of 10 min. to 15 hrs. After the reaction is complete, the reaction liquid is introduced into water or a mixture of ice and water. Alternatively, water or a mixture of ice and water can be introduced into the reaction liquid. To the aqueous mixture is then added an organic solvent to extract the reaction product with the organic solvent. The organic solvent is then distilled off to recover the reaction product. The reaction product can be purified, for instance, by recrystallization.

Further details of the ring closure reaction are described in the aforementioned Japanese Patent Provisional Publication No. 57(1982)-106678.

As described hereinbefore, the sequence of the hydrolysis and ring closure can be reversed. In more detail, the dicarboxylic acid ester of the formula (VII) is first converted into a dibenzothiepin ester derivative of the formula (IX) in the presence of a condensing agent and the dibenzothiepin ester derivative is then converted into the dibenzothiepin derivative of the formula (I) through hydrolysis. The reaction for ring closure of the dicarboxylic acid ester and the reaction for hydrolysis of the dibenzothiepin ester derivatives can be carried out almost in the same manner as described above.

The haloacetal compound of the formula (VI) can be directly converted into the dicarboxylic acid of the formula (VIII).

This reaction can be performed in a proton-donating medium in the presence of a basic compound. Examples of the proton-donating media include water, methyl alcohol, ethyl alcohol, n-propyl alcohol, isopropyl alcohol and ethylene glycol. The proton-donating medium can be used in combination with each other or in combination with other inert solvent. Other alcohol can be employed. Examples of the basic compounds include sodium hydroxice, potassium hydroxide, sodium carbonate, potassium carbonate, sodium hydrogen carbonate and potassium hydrogen carbonate. Other basic compounds can be employed.

An aqueous sodium hydroxide solution or aqueous potassium hydroxide solution is preferably employed as a combination of the proton-donating medium and the basic compound.

The basic compound is preferably employed in an amount corresponding to at least two equivalents per one equivalent of the haloacetal compound.

The reaction is generally carried out at a temperature from 50° C. to refluxing temperature for a period of 1 hour to several tens hours.

The aforementioned reaction for converting the propiophenone derivative into the haloacetal compound via the haloketone compound and the reaction for directly converting the haloacetal compound into the dicarboxylic acid can be combined to perform these reactions continuously without isolating the intermediate compounds such as the haloketone compound and haloacetal compound.

The following examples further describe the present invention.

EXAMPLE 1

(1)

Synthesis of methyl 5-(2-bromopropionyl)-2-phenylthiophenylacetate

In 300 ml of methylene chloride was dissolved 85.0 g of methyl 5-propionyl-2-phenylthiophenyl acetate. To the solution was dropwise added 40 g of bromine at room temperature. After the addition was complete, the mixture was stirred for 30 minutes. To the mixture was then added 160 ml of water. The mixture and water were well mixed by stirring, and the organic layer was separated. The organic layer was washed with water, and the organic solvent was removed under reduced pressure. To the residue was added 130 ml of methyl alcohol, and the mixture was heated to give a solution. The solution was left overnight at a temperature below 15° C., and the precipitated crystals were collected. The crystals were recrystallized from acetone-hexane to give 84 g of the desired compound, m.p. 67.5°-68.0° C.

(2)

Synthesis of methyl 5-(2-bromo-1,1-dimethoxypropyl)-2-phenylthiophenyl acetate

A mixture of 15.72 g of methyl 5-(2-bromopropionyl)-2-phenylthiophenylacetate obtained in (1) above, 12.7 g of methyl orthoformate, 0.38 g of methanesulfonic acid and 40 ml of methanol was refluxed for 24 hours and then was concentrated under reduced pressure. To the residue was added 100 ml of diethyl ether, and the mixture was washed successively with 20 ml of saturated aqueous sodium hydrogen carbonate solution, 20 ml of water, and 20 ml of saturated brine solution. The mixture was then dried over anhydrous sodium sulfate. The solvent was distilled to give a colorless oil as a residue. The oil was purified to obtain 16.85 g of methyl 5-(2-bromo-1,1-dimethoxypropyl)-2-phenylthiophenylacetate (purity 90 %) as a colorless oil.

NMR (CDCl$_3$): 1.52 (3H, d, J=8 Hz), 3.21 (3H, s), 3.35 (3H, s), 3.61 (3H, s), 3.87 (2H, s), 4.45 (1H, q, J=8 Hz), 7.1-7.5 (8H, m)

(3)

Synthesis of methyl 5-(1-methoxycarbonylethyl)-2-phenylthiophenylacetate

To methyl 5-(2-bromo-1,1-dimethoxypropyl)-2-phenylthiophenylacetate [haloacetal compound] obtained in (2) above were added 38 ml of toluene and 0.86 g of zinc bromide, and the resulting mixture was heated under reflux for 1 hour. The mixture was cooled and then 100 ml of ether was added. The resulting mixture was washed successively with 30 ml of water and 30 ml of saturated brine solution, and dried over anhydrous sodium sulfate. The solvent was distilled off, and the residue was distilled under reduced pressure to obtain 10.61 g of the desired compound (dicarboxylic acid ester) as a yellow oil (yield 77%, b.p. 212°-215° C./2 mmHg).

NMR (CDCl$_3$)δ: 1.49 (3H, d, J=7 Hz), 3.61 (3H, s), 3.67 (3H, s), 3.82 (2H, s), 3.5-3.9 (1H, m), 7.0-7.4 (8H, m)

(4)

Syntehsis of 5-(1-carboxyethyl)-2-phenylthiophenylacetic acid

To 17.2 g of methyl 5-(1-methoxycarbonylethyl)-2-phenylthiophenylacetate [dicarboxylic acid ester] obtained in (3) above was added 125 ml of 2N aqueous sodium hydroxide solution, and the resulting mixture was heated under reflux and stirring for 4 hours. After the reaction mixture was cooled, it was adjusted to pH 1 with 10% sulfuric acid, and extracted with two portions of 150 ml of methylene chloride. The organic layer was washed with 80 ml of saturated brine solution, and then was dried over anhydrous sodium sulfate. The dried layer was concentrated to dryness under reduced pressure to obtain pale brownish crude crystals. The crude crystals were recrystallized from 30 ml of 1,2-dichloroethane to obtain 14.0 g of 5-(1-carboxyethyl)-2-phenylthiophenylacetic acid as pale yellowish crystals (yield 89%), m.p. 145°-146° C.

(5)

Synthesis of 2-(10,11-dihydro-10-oxodibenzo[b,f]thiepin-2-yl)propionic acid

To a solution of 63 g of polyphosphoric acid (116%) in 63 ml of methylene chloride was added 15.8 g (0.05 mol.) of 5-(1-carboxyethyl)-2-phenylthiophenylacetic acid obtained in (4) above. The resulting mixture was stirred for 3.5 hrs. at 40° C. To the reaction solution was added a mixture of ice and water, and the resulting aqueous mixture was extracted with ethyl acetate. The extract was washed with saturated brine solution, and then dried over anhydrous sodium sulfate. The solvent was distilled off from the dried extract under reduced pressure at a temperature of lower than 40° C., and then residue was recrystallized twice from a mixture of methylene chloride and hexane to obtain 10.9 g of the 2-(10,11-dihydro-10-oxodibenzo[b,f]thiepin-2-yl)propionic acid as pale yellow crystals (yield 73%).

EXAMPLE 2

(1)

Synthesis of methyl 2-(10,11-dihydro-10-oxodibenzo[b,f]thiepin-2-yl)propionate A mixture of 0.5 g of methyl 5-(1-methoxycarbonylethyl)-2-phenylthiophenylacetate [dicarboxylic acid ester] obtained in Example 1-(3) and 5.3 g of polyphosphoric acid (116%) was stirred at a temperature of 60°–80° C. for 6 hours. The mixture was cooled, and to this was added a mixture of ice and water to decompose excessive polyphosphoric acid. The resulting mixture was extracted with ethyl acetate. The organic layer was separated and washed successively with saturated brine solution, aqueous saturated sodium hydrogen carbonate solution and saturated brine solution. The washed extract was dried over anhydrous sodium sulfate. The solvent was distilled off from the dried extract under reduced pressure, and then the residue was recrystallized from a mixture of benzene and hexane to obtain 0.4 g of methyl 2-(10,11-dihydro-10-oxodibenzo[b,f]thiepin-2-yl)propionate (yield 89%), m.p. 81.0°–82.0° C.

$IR_{max}^{neat} cm^{-1}$: 1730, 1670.

NMR (CDCl$_3$) δ: 1.44 (3H, d, J=8 Hz, —CH$_3$), 3.60 (3H, s, —CO$_2$CH$_3$), 3.66 (1H, q, J=8 Hz, —CH), 6.96–7.60 (5H, m, aromatic proton), 7.96–8.20 (1H, m, aromatic proton).

(2)

Synthesis of 2-(10,11-dihydro-10-oxodibenzo[b,f]thiepin-2-yl)propionic acid A mixture of 0.36 g of methyl 2-(10,11-dihydro-10-oxodibenzo[b,f]thiepin-2-yl)propionate, 4 ml of methanol and 3.7 ml of an aqueous solution containing 0.32 g of sodium hydrogen carbonate was heated under reflux and stirring for about 6 hours. After the reflux was complete, the mixture was cooled and shaken with 20 ml of 8% aqueous sodium hydrogen carbonate solution and 10 ml of methylene chloride. The aqueous layer was separated, made acidic by addition of conc. hydrochloric acid, and extracted with ethyl acetate. The ethyl acetate layer was shaken and washed with saturated brine solution, and then dried over anhydrous sodium sulfate. Ethyl acetate was distilled off from the dried extract under reduced pressure to obtain 0.34 g of a residue. The residue was recrystallized from a mixture of methylene chloride and hexane to obtain 0.31 g of 2-(10,11-dihydro-10-oxodibenzo[b,f]thiepin-2-yl)propionic acid (yield 90%).

EXAMPLE 3

(1)

Synthesis of methyl 5-(1-methoxycarbonylethyl)-2-phenylthiophenylacetate

To a stirred mixture of 15.72 g (50 mmol.) of methyl 5-propionyl-2-phenylthiophenylacetate, 13.32 g (125.5 mmol.) of methyl orthoformate, 20 ml of methanol and 20 ml ethylene tetrachloride was dropwise added under stirring 8.39 g (52.5 mmol.) of bromine for a period of 30 minutes. The resulting mixture was further stirred at room temperature for 30 minutes, and then was heated slowly to 110° C. for 1 hour, under distilling off materials having a low boiling point. To the reaction mixture was added 0.90 g (4.0 mmol.) of zinc bromide, and the mixture was heated to 110° C. under reflux for 3 hours. The reaction mixture was cooled, and 75 ml of water and 40 ml of methylene chloride were added. The organic layer was separated and the solvent was distilled off under reduced pressure. The residue was distilled under reduced pressure to obtain 13.78 g of the desired product as a yellow oil (yield 80%, b.p. 212°–215° C./2 mmHg).

$IR_{max}^{neat} cm^{-1}$: 1740 (C=O).

NMR (CDCl$_3$) δ: 1.49 (3H, d, J=7 Hz) 3.61 (3H, s) 3.67 (3H, s), 3.82 (2H, s), 3.5–3.9 (1H, m), 7.0–7.4 (8H, m).

(2) The above-obtained methyl 5-(1-methoxycarbonylethyl)-2-phenylthiophenylacetate was treated in the same manner as in Example 1-(4) to -(5) to obtain 2-(10,11-dihydro-10-oxodibenzo[b,f]thiepin-2-yl)propionic acid.

EXAMPLE 4

(1)

Synthesis of methyl 5-(1-methoxycarbonylethyl)-2-phenylthiophenylacetate

To a stirred mixture of 15.0 g (50 mmol.) of 5-propionyl-2-phenylthiophenylacetic acid, 13.32 g (125.5 mmol.) of methyl orthoformate, 20 ml of methanol and 20 ml ethylene tetrachloride was dropwise added under stirring 8.39 g (52.5 mmol.) of bromine for a period of 30 minutes. The resulting mixture was further stirred at room temperature for 30 minutes, and then was heated slowly to 110° C. for 1 hour, under distilling off materials having a low boiling point. To the reaction mixture was added 0.90 g (4.0 mmol.) of zinc bromide, and the mixture was heated to 110° C. under reflux for 3 hours. The reaction mixture was cooled, and 75 ml of water and 40 ml of methylene chloride were added. The organic layer was separated and the solvent was distilled off under reduced pressure. The residue was distilled under reduced pressure to obtain 12.1 g of the desired product as a yellow oil (yield 70%, b.p. 212°–215° C./2 mmHg).

$IR_{max}^{neat} cm^{-1}$: 1740 (C=O).

NMR (CDCl$_3$) δ: 1.49 (3H, d, J=7 Hz) 3.61 (3H, s) 3.67 (3H, s), 3.82 (2H, s), 3.5–3.9 (1H, m), 7.0–7.4 (8H, m).

(2) The above-obtained methyl 5-(1-methoxycarbonylethyl)-2-phenylthiophenylacetate was treated in the same manner as in Example 1-(4) to -(5) to obtain 2-(10,11-dihydro-10-oxodibenzo[b,f]thiepin-2-yl)propionic acid.

EXAMPLE 5

(1)

Synthesis of methyl 5-(1-methoxycarbonylethyl)-2-phenylthiophenylacetate

To a mixture of 157.1 g (0.50 mol.) of methyl 2-phenylthio-5-propionylphenylacetate, 133.2 g (1.255 mol) of methyl orthoformate, 200 ml of methanol and 100 ml of ethylene tetrachloride was added 2.62 g (0.040 gram atom) of zinc powder, and the mixture was heated under stirring to a temperature of 40° to 45° C. To the solution was dropped 83.6 g (0.525 mol.) of bromine for 1 hour under stirring, and then the temperature was maintained at a temperature within 42° C. and 45° C. for 30 minutes. The reaction mixture was gradually heated to raise the external temperature to 120° C., under distilling off materials having a low boiling point (b.p. 32° to 65° C.). When almost all materials having a low boiling point were distilled off and the internal temperature almost lowered to approx. 80° C., to the reaction mixture was added 100 ml of ethylene tetrachloride. Then, the mixture was again heated to raise the internal temperature to a temperature of higher than 100° C., under distilling off remaining materials having a low boiling point. After the internal temperature was kept at a temperature of 100° to 110° C. for 1 hour, the reaction mixture was cooled to approx. 50° C. To the cooled reaction mixture was added 500 ml of water, and the mixture was stirred for a while. Insoluble materials were filtered off over a Celite and then was washed with three portions of 50 ml of 1,2-dichloroethane. The organic layer was separated from the filtrate and the washings. The aqueous layer was extracted with 150 ml of 1,2-dichloroethane. The extract was combined with the above-obtained organic layer and dried over anhydrous sodium sulfate. The solvent was distilled off under reduced pressure, and then the residue was distilled under reduced pressure to obtain 141 g of the desired product as a yellow oil (yield 82%).

(2) The above-obtained methyl 5-(1-methoxycarbonylethyl)-2-phenylthiophenylacetate was treated in the same manner as in Example 1-(4) to -(5) to obtain 2-(10,11-dihydro-10-oxodibenzo[b,f]thiepin-2-yl)propionic acid.

EXAMPLE 6

(1)

Synthesis of
5-(1-carboxyethyl)-2-phenylthiophenylacetic acid

A mixture of 4.39 g (10 mmol.) of methyl 5-(2-bromo-1,1-dimethoxypropyl)-2-phenylthiophenyl acetate obtained in Example 1-(2) and 25 ml of 2N aqueous sodium hydroxide was heated under reflux and stirring for 6 hrs. The reaction mixture was cooled, adjusted to pH 6.0 with 10% sulfuric acid, and washed with two portions of 16 ml of methylene chloride. The mixture then was adjusted to pH 1 with 10% sulfuric acid and extracted with two portions of 16 ml of methylene chloride. The organic layers were combined and washed with 16 ml of water, and dried over anhydrous sodium sulfate. The solvent was then distilled off. The residual crude crystals were recrystallized from 1,2-dichloroethane to obtain 2.49 g of the desired product as white crystals (yield 79%), m.p. 145°–146° C.

(2) The above-obtained 5-(1-carboxyethyl)-2-phenylthiophenylacetic acid was treated in the same manner as in Example 1-(5) to obtain 2-(10,11-dihydro-10-oxodibenzo[b,f]thiepin-2-yl)propionic acid.

EXAMPLE 7

(1)

Synthesis of
5-(1-carboxyethyl)-2-phenylthiophenylacetic acid

A mixture of 4.39 g (10 mmol.) of methyl 5-(2-bromo-1,1-dimethoxypropyl)-2-phenylthiophenylacetate obtained in Example 1-(2), 3.45 g (10 mmol.) of anhydrous potassium carbonate, 26 ml of methanol and 13 ml of water was heated under reflux and stirring for 2 hours. The reaction mixture was distilled to remove distillates having boiling points of below 100° C. To the residue was added 10 ml of water, and the mixture was heated under reflux and stirring for 12 hrs. The reaction mixture was treated in the same manner as in Example 6-(1) to obtain 2.46 g of the desired product as white crystals (yield 78%), m.p. 145°–146° C.

(2) The above-obtained 5-(1-carboxyethyl)-2-phenylthiophenylacetic acid was treated in the same manner as in Example 1-(5) to obtain 2-(10,11-dihydro-10-oxodibenzo[b,f]thiepin-2-yl)propionic acid.

EXAMPLE 8

(1)

Synthesis of
5-(1-carboxyethyl)-2-phenylthiophenylacetic acid

A mixture of 4.39 g (10 mmol.) of methyl 5-(2-bromo-1,1-dimethoxypropyl)-2-phenylthiophenylacetate obtained in Example 1-(2), 3.45 g (25 mmol.) of anhydrous potassium carbonate, 13 ml of methanol and 13 ml of water was heated under reflux and stirring for 40 hours. The reaction mixture was treated in the same manner as in Example 6-(1) to obtain 2.41 g of the desired product as white crystals (yield 76%), m.p. 145°–146° C.

(2) The above-obtained 5-(1-carboxyethyl)-2-phenylthiophenylacetic acid was treated in the same manner as in Example 1-(5) to obtain 2-(10,11-dihydro-10-oxodibenzo[b,f]thiepin-2-yl)propionic acid.

EXAMPLE 9

(1)

Synthesis of
5-(1-carboxyethyl)-2-phenylthiophenylacetic acid

A mixture of 4.39 g (10 mol.) of 5-(2-bromo-1,1-dimethoxypropyl)-2-phenylthiophenylacetate obtained in Example 1-(2), 4.20 g (50 mmol.) of sodium hydrogen carbonate, 50 ml of ethanol and 35 ml of water was heated under reflux and stirring for 5 hours. The reaction mixture was distilled to remove distillates having a boiling point of below 100° C. The residue was then heated under reflux for 4 hours. The mixture was treated in the same manner as in Example 6-(1) to obtain 2.15 g of the desired product as white crystals (yield 68%), m.p. 145°–146° C.

(2) The above-obtained 5-(1-carboxyethyl)-2-phenylthiophenylacetic acid was treated in the same manner as in Example 1-(5) to obtain 2-(10,11-dihydro-10-oxodibenzo[b,f]thiepin-2-yl)propionic acid.

EXAMPLE 10

(1)

Synthesis of
5-(1-carboxyethyl)-2-phenylthiophenylacetic acid

To a stirred mixture of 78.6 g of methyl 5-propionyl-2-phenylthiophenylacetate, 66.3 g of methyl orthoformate, 100 ml of methanol and 50 ml ethylene tetrachloride heated to approx. 45° C. was dropwise added under stirring 40.0 g of bromine heated to the same temperature, for a period of one hour. The resulting mixture was further stirred at the same temperature for 30 minutes, and then was heated slowly to approx. 100° C. (inner temperature), under distilling off almost all materials having a low boiling point. To the reaction mixture was added 625 ml of 2N aqueous sodium hydroxide solution. The mixture was then heated under reflux and stirring for 7 hours, under distilling off ethylene tetrachloride together with water as an azeotropic mixture. The reaction mixture was cooled, and methylene chloride was added. The mixture was made acidic to pH 1 by addition of 10% sulfuric acid under stirring for extracting the reaction product with the methylene chloride. The methylene chloride layer was separated, washed with saturated brine solution and dried over anhydrous sodium sulfate. The dried methylene chloride layer was evaporated to dryness under reduced pressure to give 69.9 g of the reaction product as pale yellowish crude crystals. The crude crystals were recrystallized from 140 ml of 1,2-dichloroethane to obtain 63.2 g of the desired product (yield 80%).

(2)

Synthesis of 2-(10,11-dihydro-10-oxodibenzo[b,f]thiepin-2-yl)propionic acid

In 120 ml of dichloroethane was dissolved 45.0 g of 5-(1-carboxyethyl)-2-phenylthiophenylacetic acid obtained in (1) above under heating. To the resulting solution was added 315 g of polyphosphoric acid (105%). The was heated under an atmospheric pressure to approx. 100° C. to distilled off dichloroethane. After dichloroethane was distilled off, the mixture was cooled to approx. 80° C., and stirred at the temperature for 3.5 hours. The mixture was then cooled, and to the mixture was added 180 ml of dichloroethane. To the resulting mixture was portionwise added under stirring 180 ml of water, under keeping the mixture at 50° C. (inner temperature). The organic layer was separated, and the aqueous layer was repeatedly extracted with dichloroethane. The dichloroethane solutions were combined and dried over anhydrous sodium sulfate. The solvent was then distilled off under reduced pressure. The residue was recrystallized from a mixture of methylene chloride and n-hexane to obtain 36.3 g of the desired product (yield 86%).

We claim:

1. A process for the preparation of 2-(10,11-dihydro-10-oxodibenzo[b,f]thiepin-2-yl)propionic acid having the formula (I):

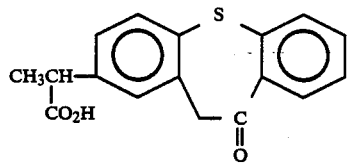

(I)

which comprises the steps:
reacting a propiophenone derivative having the formula (II):

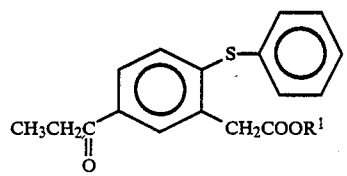

(II)

wherein $R^1$ is hydrogen or a lower alkyl group, with a halogenating agent to form a haloketone compound having the formula (III):

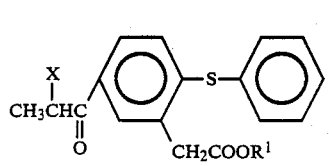

(III)

wherein $R^1$ has the same meaning as defined above; reacting the haloketone compound with a primary alcohol having the formula (IV):

$$R^2OH \qquad (IV)$$

wherein $R^2$ is a lower alkyl group, and an orthoformate having the formula (V):
$$HC(OR^2)_3 \qquad (V)$$

wherein $R^2$ has the same meaning as defined above, to form a haloacetal compound having the formula (VI):

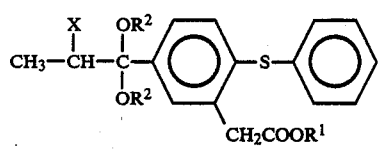

(VI)

wherein $R^1$ and $R^2$ both have the same meanings as defined above, and $R^1$ is the same as $R^2$ where $R^1$ of the formula (II) is hydrogen, and X is a halogen atom;
converting the haloacetal compound in the presence of a zinc halide into a dicarboxylic acid ester having the formula (VII):

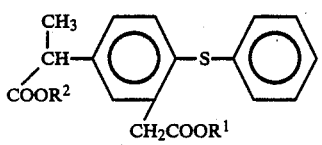

(VII)

wherein $R^1$ and $R^2$ both have the same meanings as defined above; and
hydrolyzing the dicarboxylic acid ester to give a dicarboxylic acid having the formula (VIII):

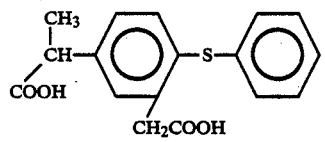

(VIII)

and
converting the dicarboxylic acid in the presence of a condensing agent into the 2-(10,11-dihydro-10-oxodibenzo[b,f]thiepin-2-yl)propionic acid.

2. The process as claimed in claim 1, wherein the halogenating agent is bromine.

3. The process as claimed in claim 1, wherein the primary alcohol is methyl alcohol and the orthoformate is methyl orthoformate.

4. The process as claimed in claim 1, wherein the zinc halide is zinc bromide.

5. The process as claimed in claim 1, wherein the conversion of the propiophenone derivative into the haloketone compound and the conversion of the haloketone compound into the haloacetal compound are continuously performed without isolating the haloketone compound.

6. The process as claimed in claim 1, wherein the conversion of the haloketone compound into the haloacetal compound and the conversion of the haloacetal compound into the dicarboxylic acid ester are continuously performed without isolating the haloacetal compound.

7. The process as claimed in claim 1, wherein the conversion of the propiophenone derivative into the haloketone compound, the conversion of the haloketone compound into the haloacetal compound, and the conversion of the haloacetal compound into the dicarboxylic acid ester are continuously performed without isolating the haloketone compound and haloacetal compound.

8. A process for the preparation of 2-(10,11-dihydro-10-oxodibenzo[b,f]thiepin-2-yl)propionic acid having the formula (I):

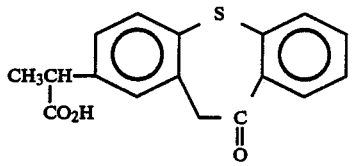
(I)

which comprises the steps:
reacting a propiophenone derivative having the formula (II):

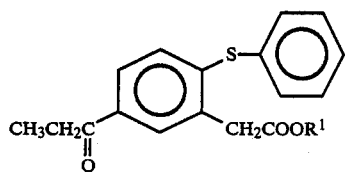
(II)

wherein $R^1$ is hydrogen or a lower alkyl group, with a halogenating agent to form a haloketone compound having the formula (III):

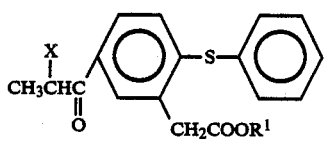
(III)

wherein $R^1$ has the same meaning as defined above;
reacting the haloketone compound with a primary alcohol having the formula (IV):

$R^2OH$ (IV)

wherein $R^2$ is lower alkyl group, and an orthoformate having the formula (V):

$HC(OR^2)_3$ (V)

wherein $R^2$ has the same meaning as defined above, to form a haloacetal compound having the formula (VI):

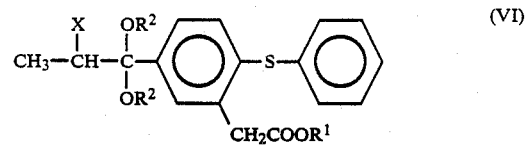
(VI)

wherein $R^1$ and $R^2$ both have the same meanings as defined above, and $R^1$ is the same as $R^2$ where $R^1$ of the formula (II) is hydrogen, and X is a halogen atom;
converting the haloacetal compound in the presence of a zinc halide into a dicarboxylic acid ester having the formula (VII):

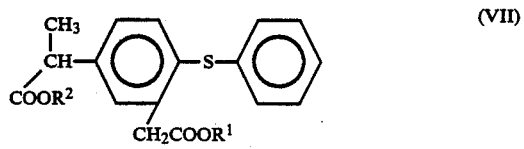
(VII)

wherein $R^1$ and $R^2$ both have the same meanings as defined above; and
converting the dicarboxylic acid ester in the presence of a condensing agent into a dibenzothiepin ester derivative having the formula (IX):

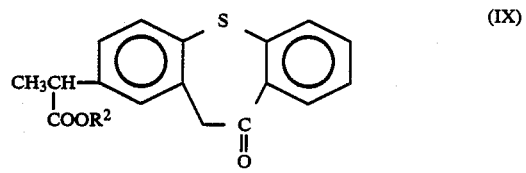
(IX)

wherein $R^2$ has the same meaning as defined above, and
hydrolyzing the dibenzothiepin ester derivative to give the 2-(10,11-dihydro-10-oxodibenzo[b,f]thiepin-2-yl)propionic acid.

9. The process as claimed in claim 8, wherein the halogenating agent is bromine.

10. The process as claimed in claim 8, wherein the primary alcohol is methyl alcohol and the orthoformate is methyl orthoformate.

11. The process as claimed in claim 8, wherein the zinc halide is zinc bromide.

12. The process as claimed in claim 8, wherein the conversion of the propiophenone derivative into the haloketone compound and the conversion of the haloketone compound into the haloacetal compound are continuously performed without isolating the haloketone compound.

13. The process as claimed in claim 8, wherein the conversion of the haloketone compound into the haloacetal compound and the conversion of the haloacetal compound into the dicarboxylic acid ester are continuously performed without isolating the haloacetal compound.

14. The process as claimed in claim 8, wherein the conversion of the propiophenone derivative into the haloketone compound, the conversion of the haloketone compound into the haloacetal compound, and the conversion of the haloacetal compound into the dicarboxylic acid ester are continuously performed without isolating the haloketone compound and haloacetal compound.

15. A process for the preparation of 2-(10,11-dihydro-10-oxodibenzo[b,f]thiepin-2-yl)propionic acid having the formula (I):

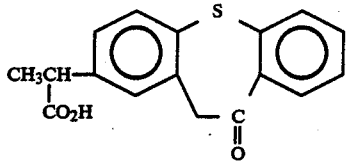
(I)

which comprises the steps:
reacting a propiophenone derivative having the formula (II):

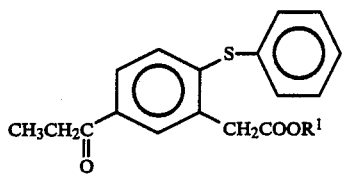
(II)

wherein $R^1$ is hydrogen or a lower alkyl group, with a halogenating agent to form a haloketone compound having the formula (III):

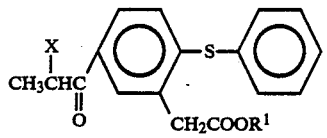
(III)

wherein $R^1$ has the same meaning as defined above; reacting the haloketone compound with a primary alcohol having the formula (IV):

  $R^2OH$ (IV)

wherein $R^2$ is a lower alkyl group, and an orthoformate having the formula (V):

  $HC(OR^2)_3$ (V)

wherein $R^2$ has the same meaning as defined above, to form a haloacetal compound having the formula (VI):

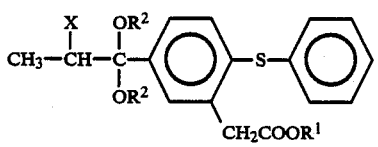
(VI)

wherein $R^1$ and $R^2$ both have the same meanings as defined above, and $R^1$ is the same as $R^2$ where $R^1$ of the formula (II) is hydrogen, and X is a halogen atom;
converting the haloacetal compound in a proton-donating medium in the presence of a basic compound into a dicarboxylic acid having the formula (VIII):

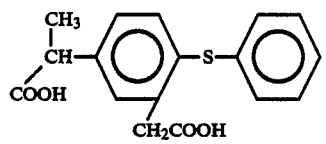
(VIII)

and
converting the dicarboxylic acid in the presence of a condensing agent into the 2-(10,11-dihydro-10-oxodibenzo[b,f]thiepin-2-yl)propionic acid.

16. The process as claimed in claim 15, wherein the halogenating agent is bromine.

17. The process as claimed in claim 15, wherein the primary alcohol is methyl alcohol and the orthformate ester is methyl orthoformate.

18. The process as claimed in claim 15, wherein the conversion of the propiophenone derivative into the haloketone compound and the conversion of the haloketone compound into the haloacetal compound are continuously performed without isolating the haloketone compound.

19. The process as claimed in claim 15, wherein the conversion of the haloketone compound into the haloacetal compound and the conversion of the haloacetal compound into the dicarboxylic acid are continuously performed without isolating the haloacetal compound.

20. The process as claimed in claim 15, wherein the conversion of the propiophenone derivative into the haloketone compound, the conversion of the haloketone compound into the haloacetal compound, and the conversion of the haloacetal compound into the dicarboxylic acid are continuously performed without isolating the haloketone compound and haloacetal compound.

21. A haloacetal compound having the formula:

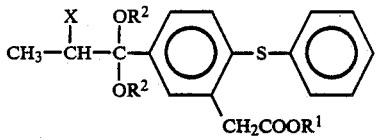

wherein $R^1$ is hydrogen or a lower alkyl group having 1-6 carbon atoms, X is a halogen atom and $R^2$ is a lower alkyl group having 1-6 carbon atoms.

22. The haloacetal compound as claimed in claim 21, wherein $R^1$ is methyl or ethyl.

23. The haloacetal compound as claimed in claim 21, wherein $R^2$ is methyl or ethyl.

* * * * *